United States Patent
Gordon et al.

(10) Patent No.: US 9,833,530 B2
(45) Date of Patent: Dec. 5, 2017

(54) VOLATILE MATERIAL DISPENSER HAVING A FACEPLATE

(71) Applicant: S.C. Johnson & Son, Inc., Racine, WI (US)

(72) Inventors: William F. Gordon, Chicago, IL (US); Thomas Jaworski, Kenosha, WI (US); Alex Mecker, Milwaukee, WI (US); Kenneth W. Michaels, Spring Grove, IL (US); Nathan P. Hendon, Franklin, WI (US); Sandrine Lebas, San Francisco, CA (US); Grace Kim, Tempe, AZ (US); Jonathan Rathbone, Chicago, IL (US); Krista Bangsund, San Francisco, CA (US); Lea Kobeli, San Francisco, CA (US); Sydney Minnis, Chicago, IL (US); In Shr Tseng, San Mateo, CA (US)

(73) Assignee: S.C. Johnson & Son, Inc., Racine, WI (US)

(*) Notice: Subject to any disclaimer, the term of this patent is extended or adjusted under 35 U.S.C. 154(b) by 754 days.

(21) Appl. No.: 13/667,157

(22) Filed: Nov. 2, 2012

(65) Prior Publication Data

US 2014/0124597 A1     May 8, 2014

(51) Int. Cl.
*A61L 9/03*     (2006.01)
*A61L 9/12*     (2006.01)

(52) U.S. Cl.
CPC ............... *A61L 9/03* (2013.01); *A61L 9/12* (2013.01); *A61L 2209/12* (2013.01); *A61L 2209/133* (2013.01)

(58) Field of Classification Search
CPC .. A61L 9/03; A61L 2209/12; A61L 2209/133; A61L 9/12
USPC .................................................. 239/34–65
See application file for complete search history.

(56) References Cited

U.S. PATENT DOCUMENTS

| | | | | |
|---|---|---|---|---|
| 4,065,261 | A | * 12/1977 | Fukada | 261/95 |
| 4,271,092 | A | * 6/1981 | Sullivan et al. | 261/30 |
| 4,523,870 | A | 6/1985 | Spector | |
| 5,370,829 | A | * 12/1994 | Kunze | 261/24 |
| 6,631,888 | B1 | * 10/2003 | Prueter | 261/30 |
| 6,854,717 | B2 | 2/2005 | Milan | |
| D508,557 | S | 8/2005 | Morrill | |
| 7,285,248 | B2 | * 10/2007 | Yamamoto et al. | 422/123 |
| D631,146 | S | 1/2011 | Shu | |
| D638,531 | S | 5/2011 | Irwin | |
| D642,667 | S | 8/2011 | Irwin | |
| D661,790 | S | 6/2012 | Majerowski | |

(Continued)

FOREIGN PATENT DOCUMENTS

| | | |
|---|---|---|
| GB | 878040 A | 9/1961 |
| WO | 03098971 A1 | 11/2003 |

(Continued)

OTHER PUBLICATIONS

PCT/US2013/067793 International Search Report and Written Opinion dated Mar. 12, 2014.

*Primary Examiner* — Chee-Chong Lee

(57) ABSTRACT

A volatile material dispenser includes a housing and a dispensing mechanism disposed within the housing for emitting a volatile material. A faceplate is attached to the housing and provides an aesthetically pleasing look to the volatile material dispenser.

20 Claims, 15 Drawing Sheets

(56) References Cited

U.S. PATENT DOCUMENTS

| | | | |
|---|---|---|---|
| D663,399 S | 7/2012 | Browder | |
| D663,404 S | 7/2012 | Browder | |
| D663,405 S | 7/2012 | Browder | |
| D663,474 S | 7/2012 | Browder | |
| D663,817 S | 7/2012 | Browder | |
| D663,818 S | 7/2012 | Browder | |
| D663,819 S | 7/2012 | Browder | |
| D663,820 S | 7/2012 | Browder | |
| D663,822 S | 7/2012 | Browder | |
| 2005/0285538 A1* | 12/2005 | Jaworski et al. | ............... 315/76 |
| 2007/0183940 A1* | 8/2007 | Yamamoto et al. | .......... 422/124 |
| 2007/0237498 A1 | 10/2007 | Helf | |

FOREIGN PATENT DOCUMENTS

| | | |
|---|---|---|
| WO | 2007110086 A1 | 10/2007 |
| WO | 2008156805 A1 | 12/2008 |
| WO | 2011019404 A2 | 2/2011 |

* cited by examiner

VOLATILE MATERIAL DISPENSER HAVING A FACEPLATE

BACKGROUND

1. Field of the Invention

The present invention relates generally to a volatile material dispenser and, more particularly, to a volatile material dispenser having a faceplate attached thereto

2. Description of the Background

Various volatile material dispensers are known in the prior art. One type of volatile material dispenser includes a housing with a refill inserted therein. The refill generally includes a container for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the manner in which the volatile material is emitted, once the volatile material has been expended from the refill, the refill is removed by a user and replaced with a new refill. Other volatile material dispensers include a housing in which the volatile material is disposed. In such volatile material dispensers, the entire housing may be disposed of and replaced.

Manufacturers of volatile material dispensers have started selling their volatile material dispensers with a faceplate attached to a portion of the housing of the dispenser. Examples of such faceplates are depicted in Morrill U.S. Design Pat. No. 508,557, Shu et al. U.S. Design Pat. No. 631,146, Irwin et al. U.S. Design Pat. No. 638,531, and Irwin et al. U.S. Design Pat. No. 642,667. Faceplates are generally used to either add décor to the volatile material dispenser or to allow a user to customize their volatile material dispenser by attaching interchangeable faceplates to the volatile material dispenser.

SUMMARY

In an illustrative embodiment, a volatile material dispenser comprises a housing and a dispensing mechanism disposed within the housing for emitting a volatile material. The volatile material dispenser further includes a faceplate attached to the housing, wherein the faceplate includes a plurality of openings creating an open area that forms at least 20% of a total surface are of the faceplate.

In a further illustrative embodiment, a volatile material dispenser comprises a housing and a dispensing mechanism disposed within the housing for emitting a volatile material. The volatile material dispenser further includes a faceplate attached to the housing wherein the faceplate includes a plurality of openings forming an open area in the faceplate, wherein at least a portion of the faceplate is spaced from the dispenser to allow air flow between the dispenser and the faceplate.

In another illustrative embodiment, a volatile material dispenser comprises a housing and a dispensing mechanism disposed within the housing for emitting a volatile material. The volatile material dispenser further includes a faceplate for attachment to the housing, wherein a volatile material output of the dispenser with the faceplate attached thereto is substantially the same as the volatile material output of the dispenser without the faceplate attached thereto.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present invention is directed to volatile material dispensers having faceplates attached thereto. While the volatile material dispensers of the present invention may be embodied in many different forms, several specific embodiments are discussed herein with the understanding that the present invention is to be considered only as an exemplification of the principles of the invention, and it is not intended to limit the invention to the embodiments illustrated.

Figure 1:
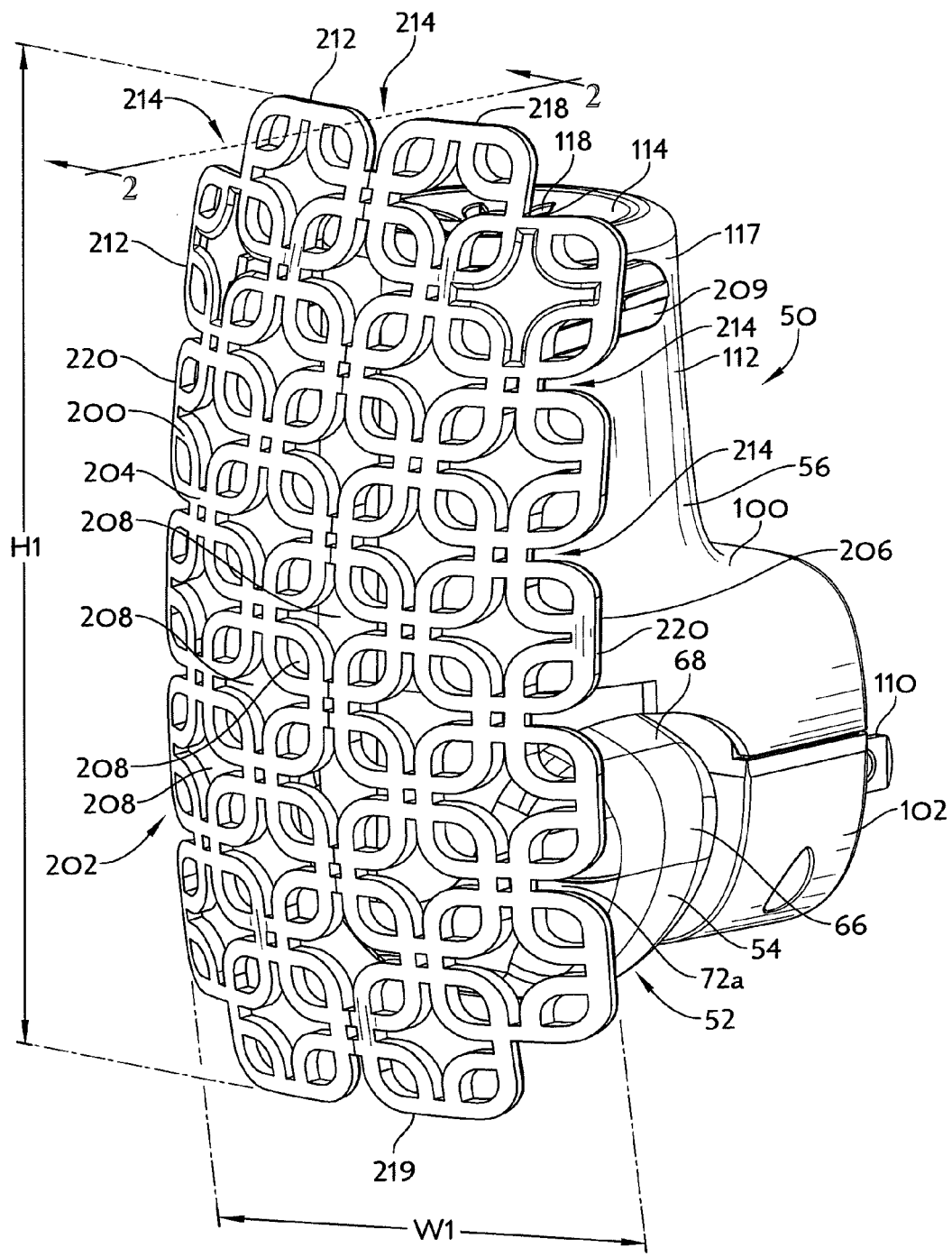
FIG. 1 is a top and front perspective view of a first embodiment of a volatile material dispenser having a first embodiment of a faceplate attached thereto.
Figure 2:
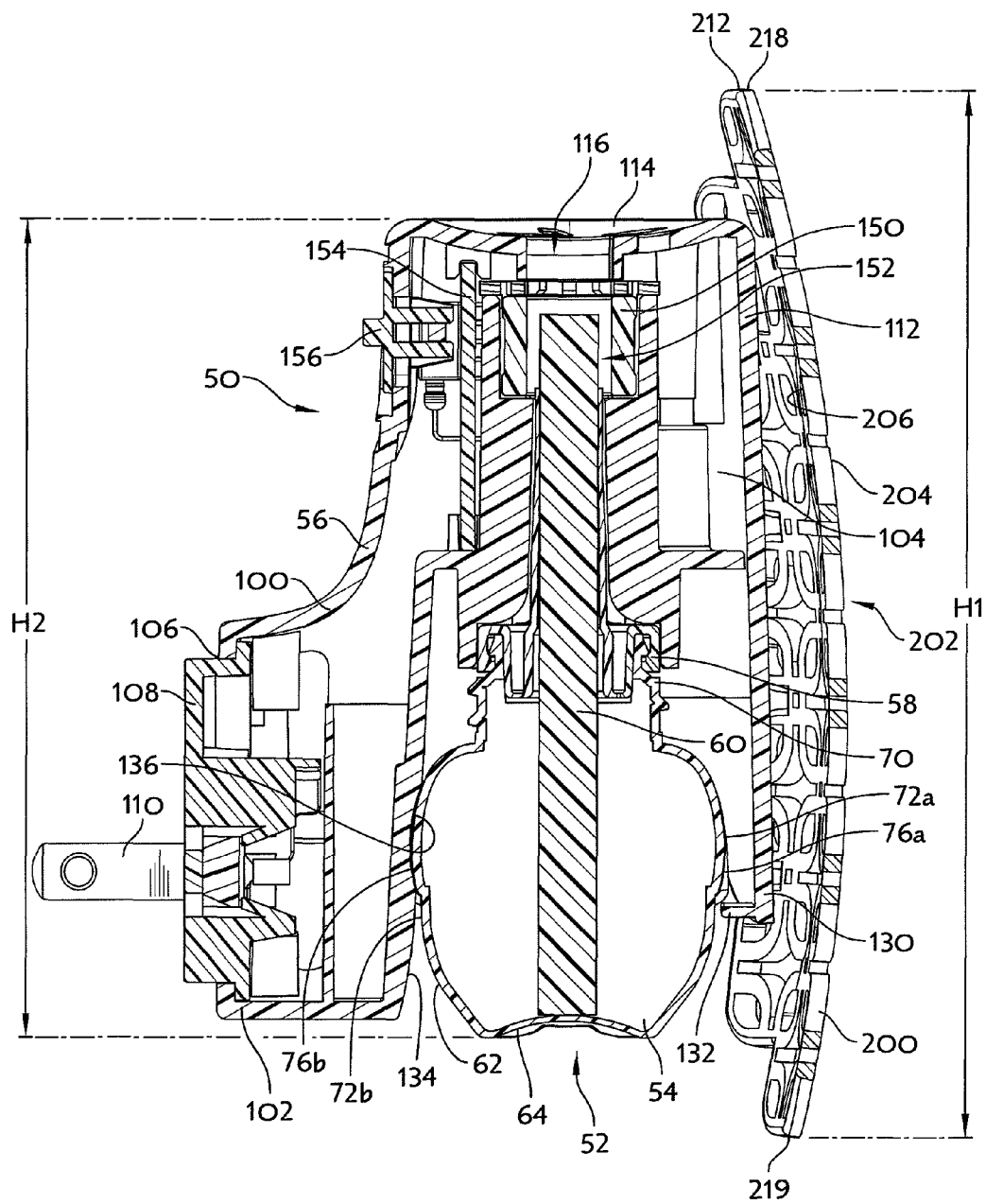
FIG. 2 is a cross-sectional view taken generally along the lines 2-2 of FIG. 1 and depicting a heater and electronic circuitry of the volatile material dispenser of FIG. 1 and further showing how the faceplate covers a housing of the volatile material dispenser.

Referring to the drawings, FIGS. 1 and 2 depict a first embodiment of a volatile material dispenser 50 adapted to accommodate a refill 52 generally including a container 54 with a volatile material therein, wherein the container 54 is adapted to be retained by a housing 56 of the volatile material dispenser 50. As seen in FIG. 2, the container 54 includes a retaining mechanism 58 for holding a wick 60 within the container 54 and a body 62 with the volatile material disposed therein. The body 62 includes a base portion 64 and opposing sidewalls 66 that extend upwardly and outwardly prior to curving inwardly toward top walls 68. The top walls 68 are integral with a neck 70. Similarly, opposing front and rear walls 72a, 72b, respectively, curve upwardly toward the neck 70.

As seen in FIG. 2, the neck 70 of the refill 52 includes a threaded portion disposed on an outer surface thereof and an opening disposed through a top portion thereof, wherein the opening allows access to the volatile material. The retaining mechanism 58 is disposed within the neck 70. The container 54 further optionally includes raised portions 76a, 76b extending outwardly from one or more of the opposing front and rear walls 72a, 72b. In one embodiment, the raised portions 76a, 76b are in the form of inverted shell-shaped members.

The volatile material disposed in the container 54 may be any type of volatile material adapted to be dispensed into an environment. For example, the container 54 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances and/or preservatives.

Turning again to FIGS. 1 and 2, the housing 56 of the volatile material dispenser 50 generally includes upper and lower portions 100, 102 attached to one another to form an interior chamber or cavity 104 therebetween. The upper and lower portions 100, 102 also join to form an aperture 106 at a rear portion of the housing 56 through which a plug assembly 108 extends. The plug assembly 108 includes two electrical prongs 110 adapted for insertion into a convention outlet. While the plug assembly 108 is shown as being a conventional plug assembly for the United States, a plug assembly adapted for use in any other country may be utilized. In addition, the plug assembly 108 may include any features known in the art, for example, the plug assembly 108 may be partially or fully rotatable.

Figure 3:
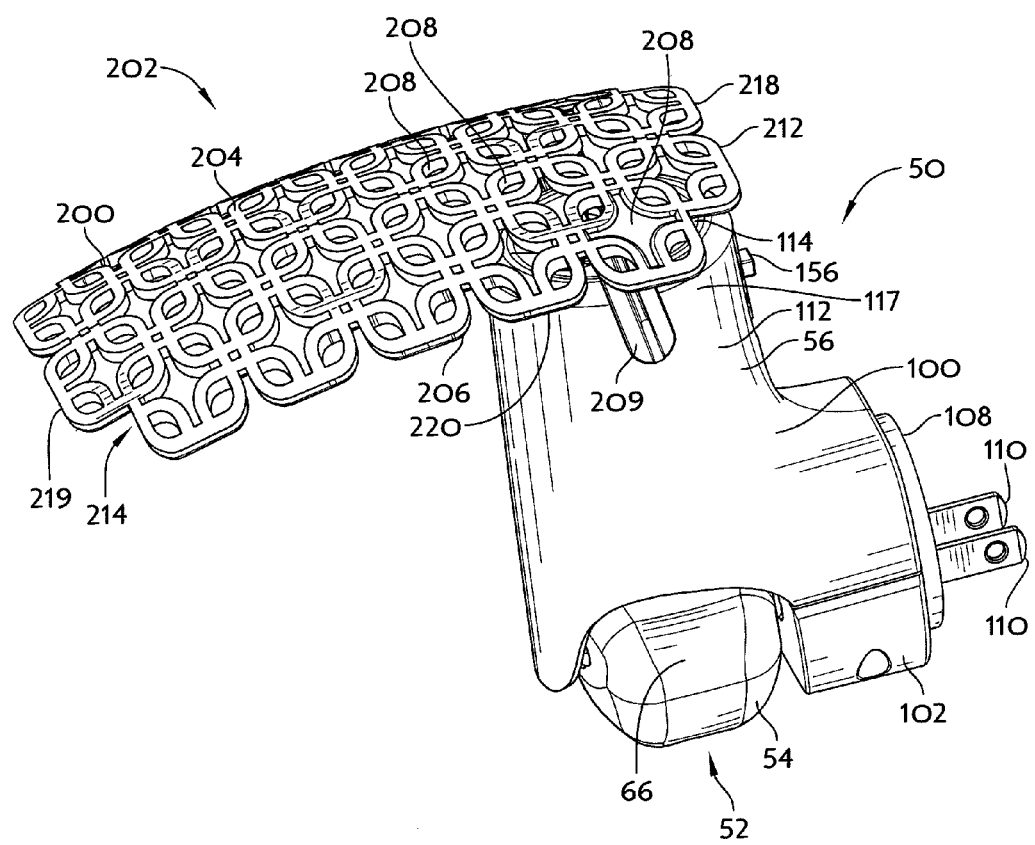
FIG. 3 is a top and front perspective view of the volatile material dispenser and the faceplate of FIG. 1 with the faceplate rotated to a position in which a refill disposed within the volatile material dispenser may be accessed.

The upper portion 100 of the housing 56, as best seen in FIG. 3, includes a generally cylindrical side wall 112 curving outwardly toward the plug assembly 108 and a top wall 114 that encloses the side wall 112. The top wall 114 includes a central aperture 116 and a plurality of peripheral apertures 118 spaced from a periphery of the central apertures 116. Each of the apertures 116, 118 provides a means by which air and vaporized volatile material may move out of the housing 56. Two opposing circular recesses 115 extend through the cylindrical side wall 112 on opposing sides 117 of the housing 56. While the recesses 115 are shown as being adjacent the top wall 114, the recesses 115 may be disposed at any point along a height of the side wall 112. As discussed below, positioning the recesses 115 adjacent the top wall 114 facilitates rotational movement of a faceplate 200.

Referring to FIG. 2, a retaining wall 130 extends downwardly from a front portion of the cylindrical wall 112 to partially enclose the refill 52 when disposed within the housing 56. The retaining wall 130 includes an inwardly extending lip 132 that aids in retaining the refill 52. The lower portion 102 of the housing 56 includes an outwardly facing wall 134 having a recess 136. When a refill is inserted into the housing 56, a first of the raised portions 76 is disposed within the recess 136 and a second of the raised portions 76 sits on the inwardly extending lip 132. The refill 52 may be removed from the housing 56 by pulling downwardly on the refill 52. Alternatively, the refill 52 may be attached to the housing 56 in any other suitable manner.

A heater 150 is disposed within the housing 56, as best seen in FIG. 2. When the refill 52 is inserted into the housing 56, the wick 60 is inserted into a channel 152 through the heater 150 to vaporize volatile material that is moved by capillary action from the container 54 into the wick 60. While the heater 150 is depicted as a ring heater, the heater 150 may be replaced by any other suitable heating mechanism or a different dispensing mechanism.

The volatile material dispenser 50 further includes a circuit board 154 including suitable electronic circuitry for operating the volatile material dispenser 50. For example, the heater 150 is connected to the circuit board 154 and a switch 156 may also be connected to the circuit board 154 to operate the heater 150. For example, the switch 156 may change a temperature of the heater 150, change a vaporization rate of the heater 150, or may change any other feature or function of the heater 150 (or any other component of the volatile material dispenser 50). The circuit board 154 is connected by wires to the plug assembly 108, such that energy provided to the electrical prongs 110 powers the dispenser 50. Alternatively, the circuit board 154 may be omitted and the heater 150 and/or other electrical components may be connected directly to the electrical prongs 110.

Referring again to FIGS. 1 and 2, the volatile material dispenser 50 includes a faceplate 200 having a plurality of segments forming a pattern 202 that extends between front and rear surfaces 204, 206 of the faceplate 200. The pattern 202 is formed by a plurality of openings 208 (only some of which are labeled). Resilient arms 209 extend outwardly from the rear surface 206 of the faceplate 200 and include inwardly extending posts 210. As can be seen in FIG. 3, the resilient arms 209 may be pulled outwardly such that the posts 210 can pass the sides 117 of the housing 56. The arms 209 are released once the posts 210 are aligned with the recesses 115 in the sides 117 of the housing 56, such that the posts 210 enter and are retained within the recesses 115. While arms 209 and posts 210 are depicted herein as detachably attaching the faceplate 200 to the volatile material dispenser 50, any other suitable attachment mechanism may be utilized.

The openings 208 in the faceplate 200 represent an open surface area of about 4.0 square inches and solid segments of the pattern 202 represent about 7.6 square inches. A total surface area of faceplate including the open surface area and the pattern is about 11.6 square inches. The open area is therefore about 35% of the total surface area of the faceplate 200. In some embodiments, the open area may be between about 20% and about 50% of the total area of the faceplate 200. In further embodiments, the open area may be between about 30% and about 40% of the total area of the faceplate 200. The open area should be great enough to provide air flow and prevent insulation, but should be small enough to hide enough of the dispenser 50 that the dispenser 50 is not easily seen through the open area. While two patterns are depicted herein, other patterns are possible without departing from the scope of the present invention.

Most of the commercially available faceplates are solid constructs that are attached to an underlying volatile material dispenser with minimal or no gap therebetween (as a "skin" to the underlying device). Such commercial faceplates do not have much (if any) open area in their construction. The open area of the embodiments disclosed herein provide better air flow and less insulation for the dispenser 50. First, the open area and design of the faceplates herein communicate "fragrancing" and "air flow" to the consumer by providing a 3-dimensional construct that animates the air flow in the mind of the consumer. Open area connotes more air flow to the consumer and more air flow connotes more fragrancing. Additionally, the open area communicates air flow through and around the dispenser 50, rather than acting as a cover or shield that could stifle such air flow and/or emission of volatile material.

By utilizing open area in the design of the faceplates herein, the faceplates are perceived as being smaller than a similar size faceplate without such open area. Thus, the faceplate can be large enough to wrap around a dispenser and hide the refill without being perceived as big and bulky.

The open area is believed to provide better air flow and less insulating character than faceplates that are closely fit to the size and shape of the underlying volatile material dispenser. Testing of dispensers with tight-fitting faceplates showed faster use up of refills versus the same dispenser without such faceplates. It is believed that the dispensers with tight-fitting faceplates run hotter and, therefore, use volatile material more quickly and alter the performance of the dispenser. It is therefore believed that, when the faceplates disclosed herein are spaced away from the underlying dispenser and include the open area in the design, the dispensers to which the faceplates are attached will operate at the same or a cooler temperature than dispensers without faceplates. In this manner, it is believed that the fragrance performance will not be affected by the faceplates disclosed herein, as is the case with prior-art tight-fitting faceplates. It is also believed that the output rate of the dispensers disclosed herein would be the same regardless of whether the faceplate is attached to the dispenser.

As can be seen in FIGS. 1 and 2, the faceplate 200 has an outer peripheral edge 212 that is not well-defined or linear. Rather, the outer peripheral edge 212 has broken edges or cutouts 214 (only some of which are labeled) that create a discontinuous outer peripheral edge 212. By breaking the outer peripheral edge 212 of the faceplate 200, the faceplate 200 can more easily blend into the décor of a home or other environment. The faceplate 200 aids in camouflaging the dispenser 50 because the cutouts 214 do not provide an observer's eye with as much of a distinct feature on which to focus, as compared to sharp, distinct edges that are easily recognizable as a volatile material dispenser.

The faceplate 200 may also have a height dimension H1 (FIGS. 1 and 2) that is greater than a combined height H2 of the dispenser 50 and the refill 52 and a width dimension W1 (FIG. 1) that is greater than a width of the dispenser 50. Further, a top edge 218 of the faceplate 200 may extend to or beyond a top of the dispenser 50, a bottom edge 219 of the faceplate 200 may extend to or beyond a bottom of the dispenser 50 and/or the refill 52, and outermost side edges 220 of the faceplate 200 extend to or beyond the dispenser 50 and/or the refill 52. The size and extent of the faceplate 200 further aids in hiding, masking, and/or camouflaging the underlying dispenser 50.

The faceplate 200 has a curvature from top to bottom, as seen in FIG. 2, and from side to side, as seen in FIG. 1, that at least partially wraps around, covers, and masks a front portion of the housing 56 and the refill 52. In this manner, the faceplate 200 blocks the view of the dispenser 50 and the refill 52 when viewed from a front of the dispenser 50 and dramatically alters the appearance of the dispenser 50 by setting itself off from the dispenser 50 and screening the dispenser 50. The faceplate 200 provides a more attractive design that does not look like a volatile material dispenser. By contrast, faceplates used on current commercial devices employing faceplates do not alter the appearance of the dispenser, but instead merely put a new skin or decoration on the dispenser. Such commercial faceplates may add color or images, but they still give the appearance of a volatile material dispenser. By screening the dispenser and refill, the faceplates herein add décor and divert attention from elements that communicate to the consumer or guests in the consumer's home that the object is a volatile material dispenser. Optionally, although the faceplate 200 is shown as being curved around the dispenser 50, the faceplate 200 may include multiple surfaces that are angled with respect to one another and which wrap around portions of the dispenser 50.

As further seen in FIG. 2, the faceplate 200 is spaced a distance from a front portion of the cylindrical wall 112 of the housing 56. Due to the curvature of the faceplate 200, the faceplate 200 is spaced a greater distance from the cylindrical wall 112 at a central portion 216 of the faceplate 200 and a less distance from the cylindrical wall 112 at the top and bottom edges 218, 219 of the faceplate 200. Regardless, the rear surface 206 of the faceplate 200 does not contact the cylindrical wall 112. In an illustrative embodiment, the faceplate 200 may be disposed at least 1 millimeter from the dispenser 50. The open area of the faceplate 200 in combination with the faceplate 200 being spaced from the cylindrical wall 112 create an air gap between the faceplate 200 and the dispenser 50. In this manner, the faceplate 200 does not act as an insulator and therefore, does not increase a temperature within the dispenser 50, which would increase an output or emission rate of the dispenser 50. An output or emission rate of the dispenser 50 is left unchanged with the addition of the faceplate 200.

As seen in FIG. 3, the retention of the posts 210 extending from the arms 209 within the recesses 115 in the opposing sides 117 of the housing 56 allow the faceplate 200 to be rotated. As seen in FIG. 1, the size and shape of the faceplate 200 prevent easy access to the refill 52 when the faceplate is in position spaced from the cylindrical wall 112. A user may therefore rotate the faceplate 200 about the posts 210 (that are in the recesses 115) until a top edge 218 of the faceplate 200 hits the top wall 114 of the dispenser 50 and the faceplate 200 is in an open position, as seen in FIG. 3. Alternatively, the recesses 115 and the posts 210 may include one or more features that provide a stop for halting rotation of the faceplate 200 into the open position and/or holding the faceplate 200 in the open position so a user can view, remove, and/or replace the refill 52. When in the open position, a user may easily view the refill 52 to determine whether the refill 52 needs to be replaced and/or may easily remove the refill 52 and/or replace it with another refill 52.

The recesses 115 and/or posts 210 may also include a feature that stops rotation of the faceplate 200 into a closed position, as seen in FIG. 1. Alternatively, a stop, such as a post or projection may extend outwardly from the front portion of the cylindrical wall 112 or the rear surface 206 of the faceplate 200 to stop rotation (prevent over-rotation) of the faceplate 200 and position the faceplate 200 in a generally vertical orientation away from the dispenser 50 and/or the refill 52, as seen in FIG. 2. The stop may also aid in spacing the faceplate 200 from the cylindrical wall 112 and the refill 52. While the faceplate 200 is shown as being spaced from the refill 52, in alternative embodiments, the faceplate 200 may contact the refill 52. In one embodiment, the refill 52 may act as a stop for rotation of the faceplate 200 into the closed position.

While one particular mechanism for attaching the faceplate 200 to the dispenser 50 is depicted herein, other suitable attachment mechanisms are contemplated. Example attachment mechanisms include, but are not limited to, recesses within the arms 209 of the faceplate 200 and projections extending outwardly from the cylindrical wall 112 of the housing 56, an engagement mechanism that allows the faceplate 200 to slide vertically up and down, a magnetic attachment, a fixed hinge at a top of the dispenser 50, a fixed hinge on a side of the dispenser 50, a fixed hinge on a bottom of the dispenser 50, a double-jointed faceplate, or a rubber band attachment.

The faceplate 200 may be removably attached to the dispenser 50 such that the faceplate 200 may be replaced with faceplates having other designs (e.g., décor, seasonal, novelty, etc.). However, the connection between the faceplate 200 and the dispenser 50 is preferably strong enough to secure the faceplate 200 in place during use, during rotation of the faceplate 200, and during insertion of and removal of the dispenser 50 from an electrical outlet.

The faceplate 200 may be made of a material similar to the dispenser 50 to which it is connected, for example, a thermoplastic material. Optionally, the faceplate 200 may be made of other materials, for example, cardboard, card stock, heavier paper stock, metal, wood, bamboo, or any other suitable material or combinations thereof. Inexpensive materials, such as paper, would allow for frequent design changes and/or options and consumer-designed or decorated options.

Figure 4:
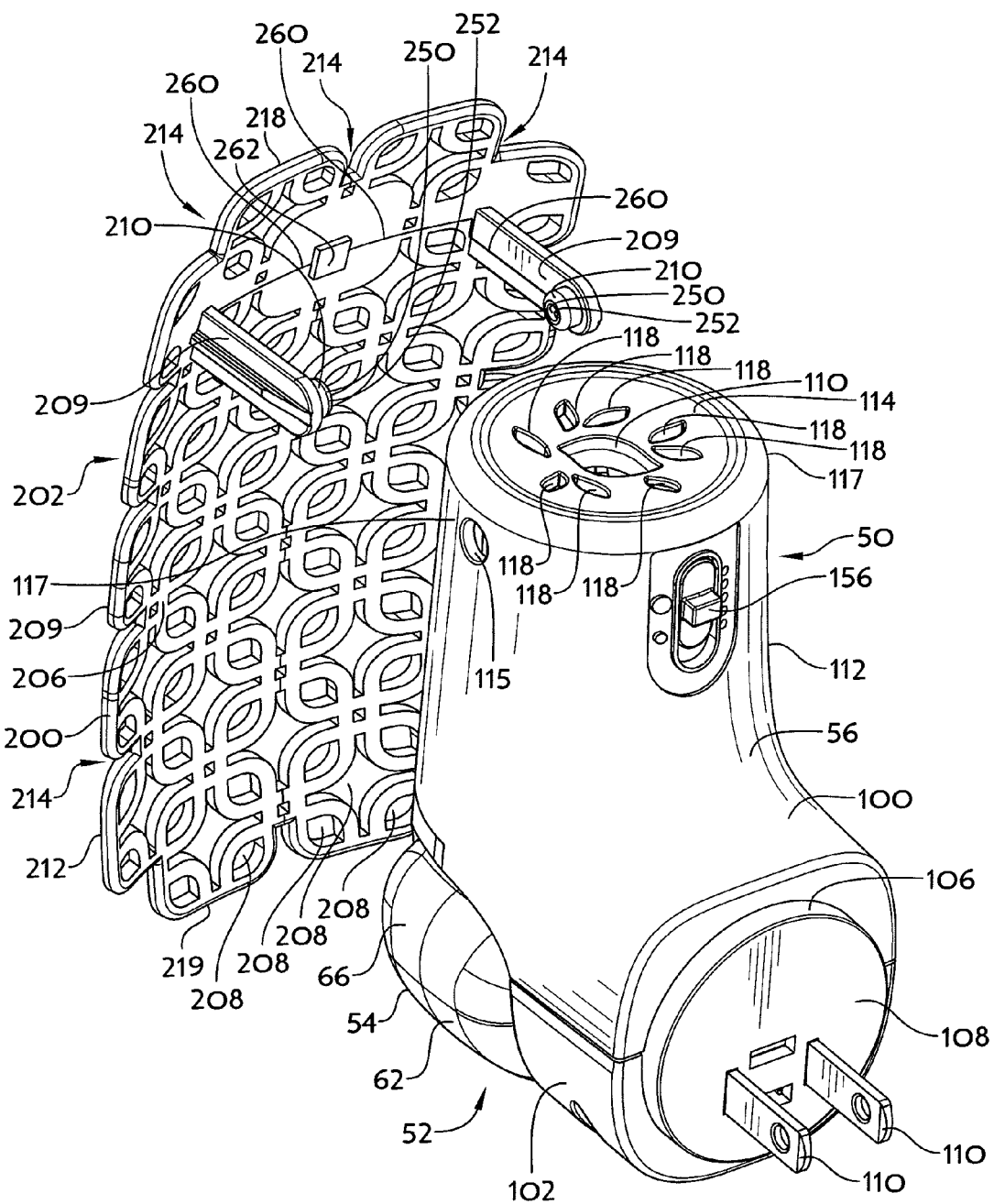
FIG. 4 is a rear and top, partially exploded perspective view of the volatile material dispenser and the faceplate of FIG. 1.
Figure 5:
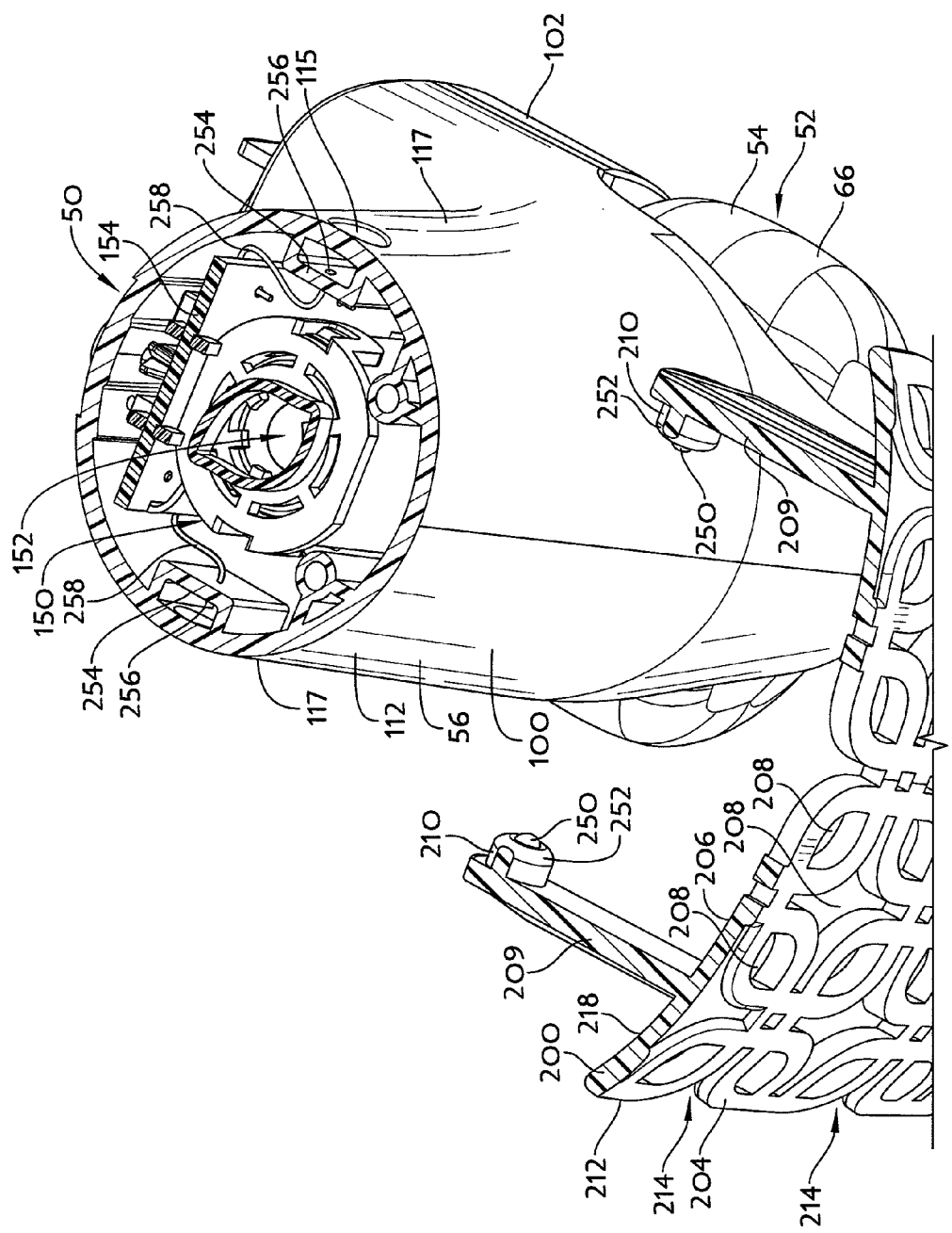
FIG. 5 is a top, partially exploded, cutaway perspective view of the volatile material dispenser of FIG. 1 with a top wall of the volatile material removed to view internal components of the volatile material dispenser.

The faceplate 200 may include any number of features. Referring to FIGS. 4 and 5, the posts 210 of the faceplate 200 may include contacts 250 on ends 252 thereof. Similarly, the dispenser 50 may include surfaces 254 spaced inwardly from the cylindrical wall 112 of the housing 56 and aligned with the recesses 115, wherein contacts 256 are positioned on the surfaces 254. The contacts 256 are connected by wires 258 or another suitable connection to the circuit board 154 to provide power thereto. Similarly, wires 260 may extend from the contacts 250 to any portion of the faceplate 200 to power one or more electronic components 262 located on the faceplate 200. The wires 260 may be attached to or located within the arms 209 and/or portions of the faceplate 200. When the posts 210 are positioned within the recesses 115, the contacts 250 on the posts 210 contact the contacts 256 on the surfaces 245, thereby allowing the flow of electricity into the wires 260.

Figure 6:
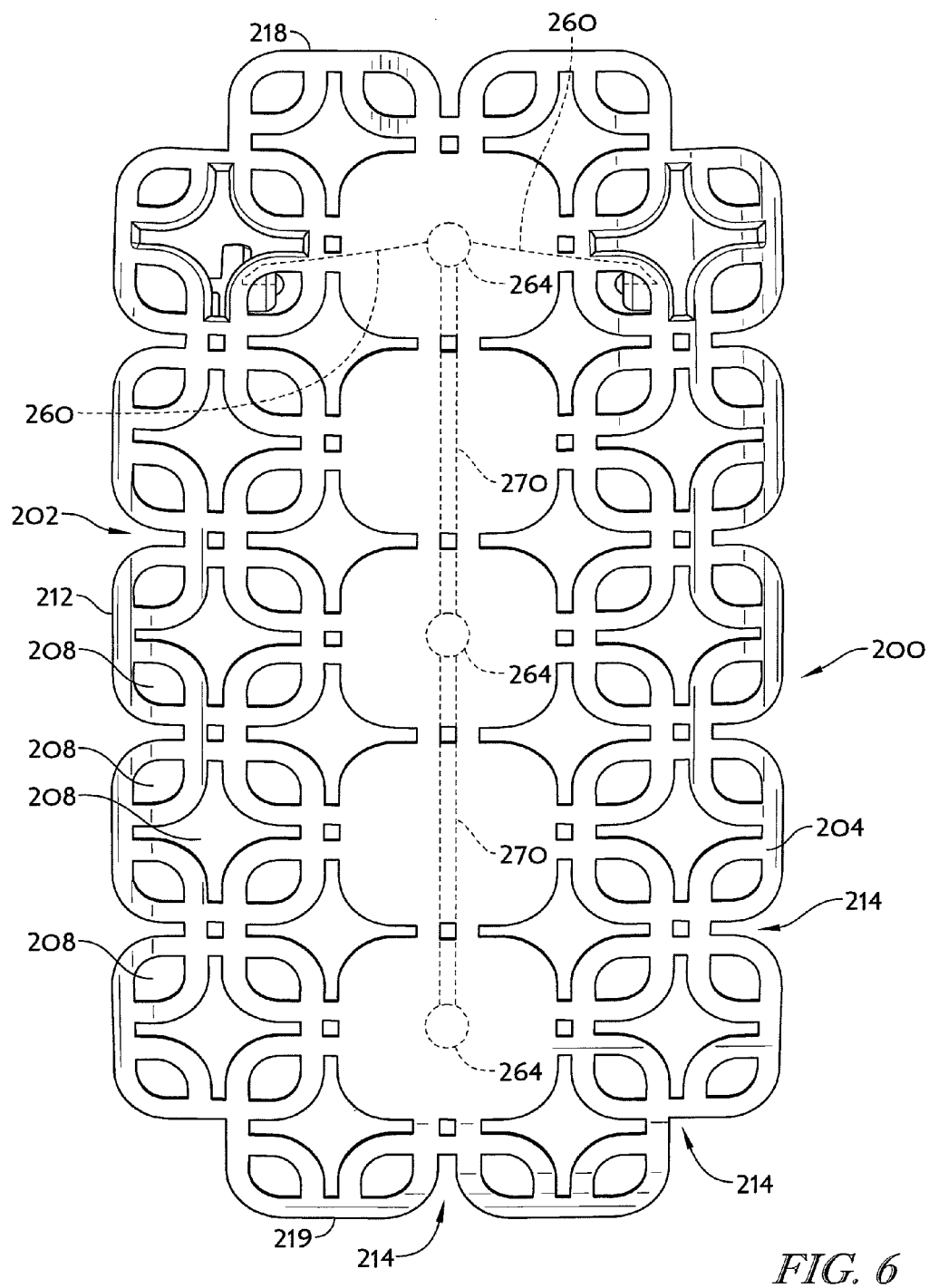
FIG. 6 is a front elevational view of the faceplate of FIG. 1, wherein the faceplate has been modified to include a plurality of light sources.

As seen in FIG. 4, the wires 260 may extend to the one or more electrical components 262, such as one or more light sources, one or more fans, one or more additional volatile material dispensing components, a messaging unit or display device, or any other electrical component. If a light source is utilized, the light source may include one or more of a light emitting diode (LED), an incandescent light source, an electroluminescent light source, a fluorescent light source, a neon light source, or any other suitable light source. In one embodiment, as seen in FIG. 6, the electrical component 262 may comprise a plurality of light sources 264 on a rear surface 206 of the faceplate 200. A first of the light sources 264 may be electrically connected to the wires 260 and the other light sources 264 may be electrically connected by additional wires 270 to one another. If light sources 264 (or other electrical components) are utilized, one or more sections of the faceplate 200 may be solid to allow the light sources 264 to shine through solid material forming the faceplate 200. The light sources 264 may provide an indicator or notification (e.g., that a refill needs to be replaced), may provide backlighting, may act as a night light, may provide a light show, may provide seasonal lighting, may be for decorative purposes, and/or may provide any other suitable function.

While one manner of illuminating the faceplate 200 is described, the faceplate 200 may be illuminated in many different ways. For example, the light source(s) 264 may glow directly through the faceplate 200, or the faceplate 200 may serve as a lightpipe.

Figure 7:
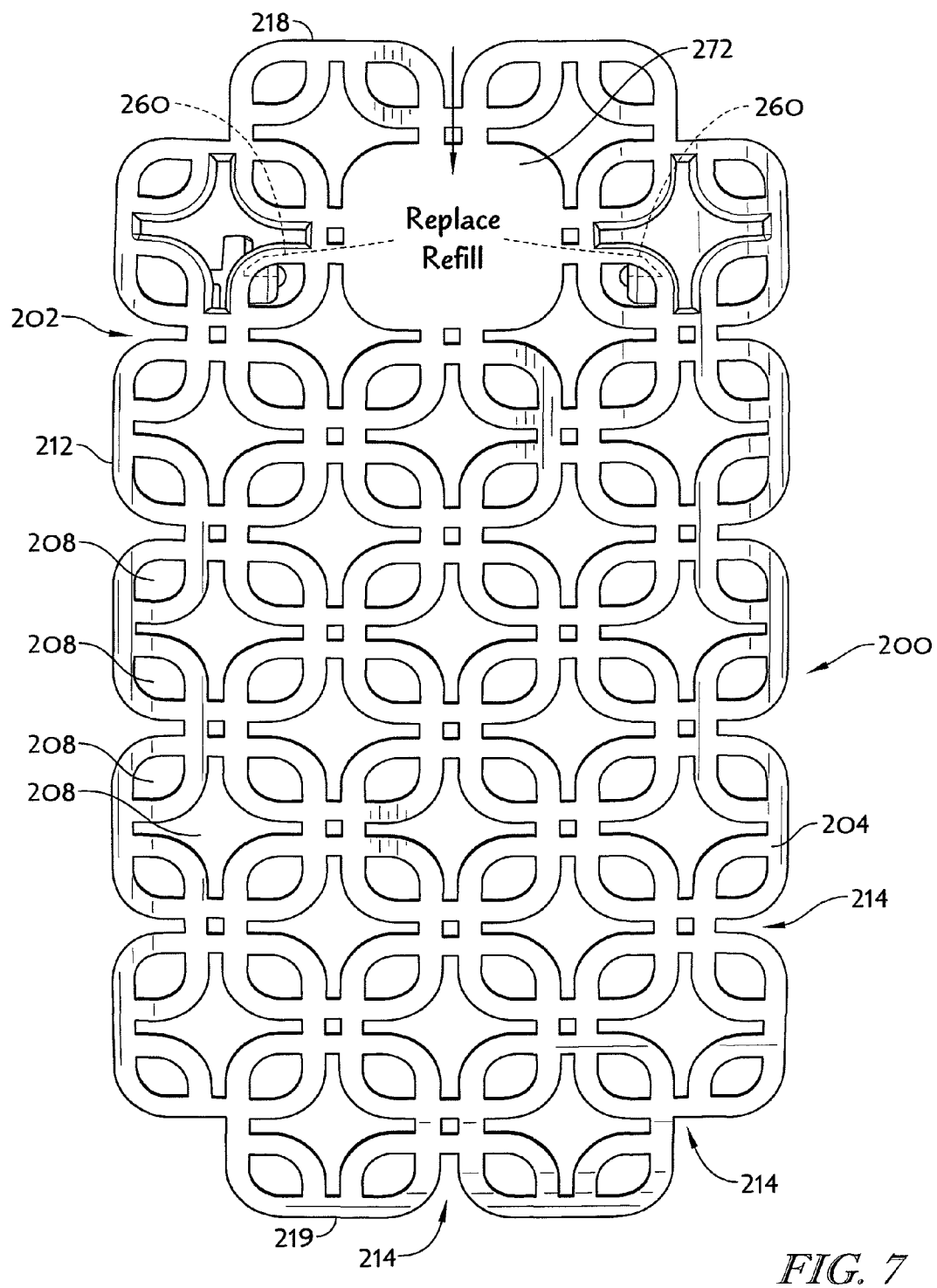
FIG. 7 is a front elevational view of the faceplate of FIG. 1, wherein the faceplate has been modified to include a message that may be displayed on the faceplate.

In the embodiment of FIG. 7, the electrical component 262 may be in the form of an electronic or digital display 272 that is electrically connected to the wires 260. The digital display 272 may be used with or without light sources 264 and may be programmed to continuously or periodically display a message, design, and/or other indicia. In one illustrative embodiment, as seen in FIG. 7, the message may read "Replace Refill." The dispenser 50 may be programmed to determine when the refill 52 needs to be replaced and display the "Replace Refill" message upon depletion of volatile material within the refill 52. Alternatively, or in addition, the faceplate 200 and/or dispenser 50 may include an audible signal in the form of a buzzer, speaker, or other audible signal to alert a user of a condition, for example, refill status.

Figure 8:
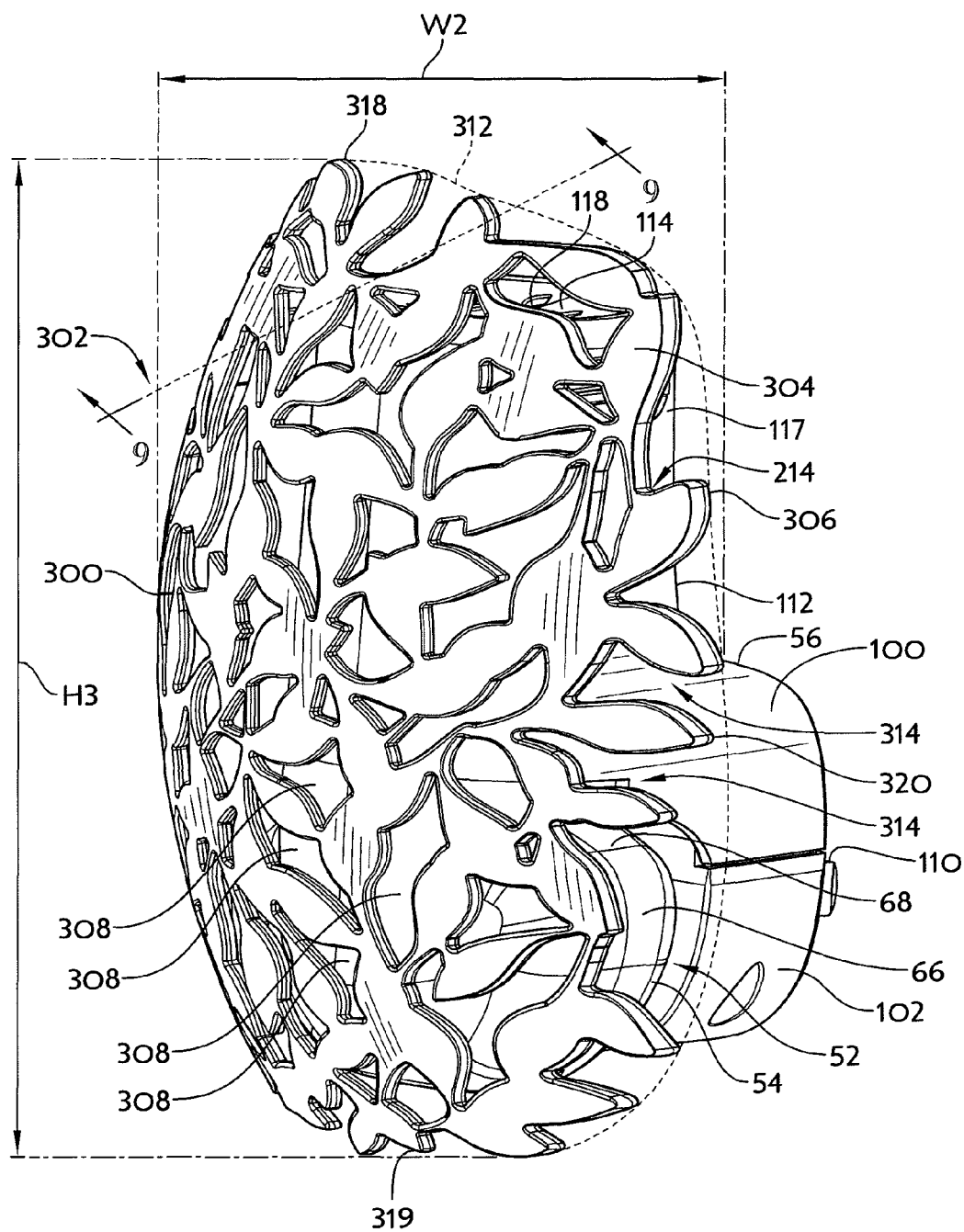
FIG. 8 is a top and front perspective view of the volatile material dispenser of FIG. 1 having a second embodiment of a faceplate attached thereto.
Figure 9:
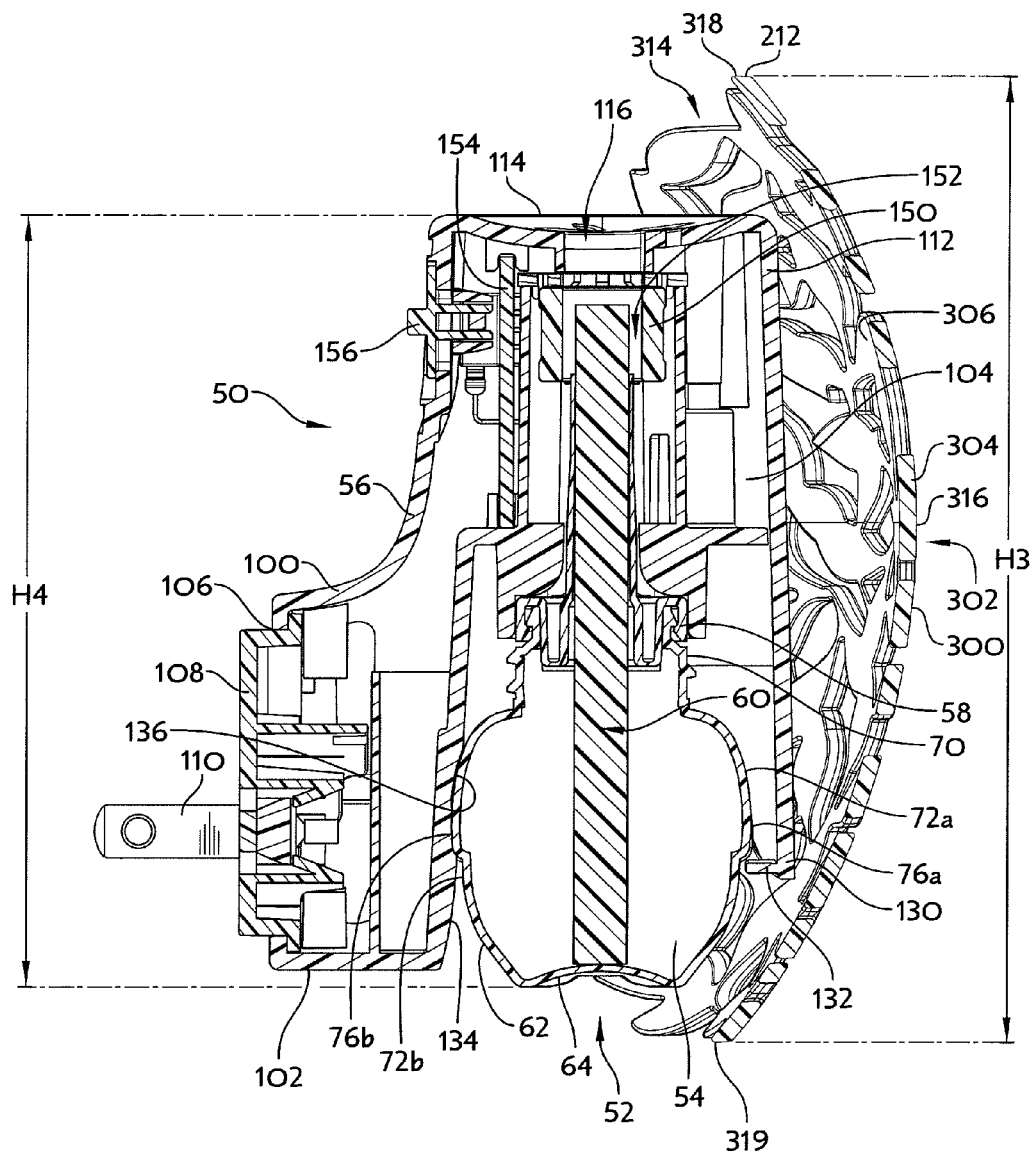
FIG. 9 is a cross-sectional view taken generally along the lines 9-9 of FIG. 8 and depicting a heater and electronic circuitry of the volatile material dispenser of FIG. 8 and further showing how the faceplate is spaced from a housing of the volatile material dispenser.

A second embodiment of a faceplate 300 is depicted in FIGS. 8 and 9 on the volatile material dispenser 50. The faceplate 300 is similar to the faceplate 200 and includes a pattern 302 that resembles leaves or a pattern that mimics the look of nature. The pattern 302 that extends between front and rear surfaces 304, 306 of the faceplate 300 and is formed with a plurality of openings 308 (only some of which are labeled). The faceplate 300 also includes arms 209 and posts 210 that may be identical to those of the faceplate 300. Similar to the embodiment of FIGS. 1 and 2, the openings 308 in the faceplate 300 represent an open surface area of about 4.8 square inches and solid segments of the pattern 302 represent about 8.5 square inches. A total surface area of the faceplate 300 is about 13.3 square inches and, therefore, the faceplate 300 has an open area of about 36%. Beyond the pattern formed in the faceplate 300, the functionality of the faceplate 300 is identical to the faceplate 200 of FIGS. 1 and 2. Further, any of the features described with relation to the dispenser 50 and/or the faceplate 200 may be implemented within the embodiment of FIGS. 8 and 9.

Similar to the faceplate 200, the faceplate 300 has an outer peripheral edge 312 (shown best in dashed lines in FIG. 8) that is not well-defined or linear. Rather, the outer peripheral edge 312 has broken edges or cutouts 314 (only some of which are shown) that create a discontinuous outer peripheral edge 312. By breaking the outer peripheral edge 212 of the faceplate 300, the faceplate 300 can more easily blend into the décor of a home or other environment and mimic the look of nature, for example. The faceplate 300 aids in camouflaging the dispenser 50 because the cutouts 314 do not provide an observer's eye with as much of a distinct feature on which to focus, as compared to sharp, distinct edges that are easily recognizable as a volatile material dispenser.

The faceplate 300 may also have a height dimension H3 (FIGS. 8 and 9) that is greater than a combined height H4 of the dispenser 50 and the refill 52 and a width dimension W2 (FIG. 8) that is greater than a width of the dispenser 50. Further, a top edge 318 of the faceplate 300 may extend to or beyond a top of the dispenser 50, a bottom edge 319 of the faceplate 300 may extend to or beyond a bottom of the dispenser 50 and/or the refill 52, and outermost side edges 320 of the faceplate 300 may extend to or beyond the dispenser 50 and/or the refill 52. The size and extent of the faceplate 300 further aids in hiding, masking, and/or camouflaging the underlying dispenser 50.

The faceplate 300 has a curvature from top to bottom, as seen in FIG. 9, and from side to side, as seen in FIG. 8, that at least partially wraps around, covers, and masks a front portion of the housing 56 and the refill 52. In this manner, the faceplate 300 blocks the view of the dispenser 50 and the refill 52 when viewed from a front of the dispenser 50 and dramatically alters the appearance of the dispenser 50 by setting itself off from the dispenser 50 and screening the dispenser 50. The faceplate 300 provides a more attractive design that does not look like a volatile material dispenser, in a manner similar to the faceplate 200. Optionally, although the faceplate 300 is shown as being curved around the dispenser 50, the faceplate 300 may include multiple surfaces that are angled with respect to one another and which wrap around portions of the dispenser 50.

As further seen in FIG. 9, the faceplate 300 is spaced a distance from a front portion of the cylindrical wall 112 of the housing 56. Due to the curvature of the faceplate 300, the faceplate 300 is spaced a greater distance from the cylindrical wall 112 at a central portion 316 of the faceplate 300 and a less distance from the cylindrical wall 112 at the top and bottom edges 318, 319 of the faceplate 300. Regardless, the rear surface 306 of the faceplate 300 does not contact the cylindrical wall 112. In an illustrative embodiment, the faceplate 200 may be disposed at least 1 millimeter from the dispenser 50. The open area of the faceplate 300 in combination with the faceplate 300 being spaced from the cylindrical wall 112 create an air gap between the faceplate 300 and the dispenser 50. In this manner, the faceplate 300 does not act as an insulator and therefore, does not increase a temperature within the dispenser 50, which would increase an output or emission rate of the dispenser 50. An output or emission rate of the dispenser 50 may be left unchanged with the addition of the faceplate 300.

Figure 10:
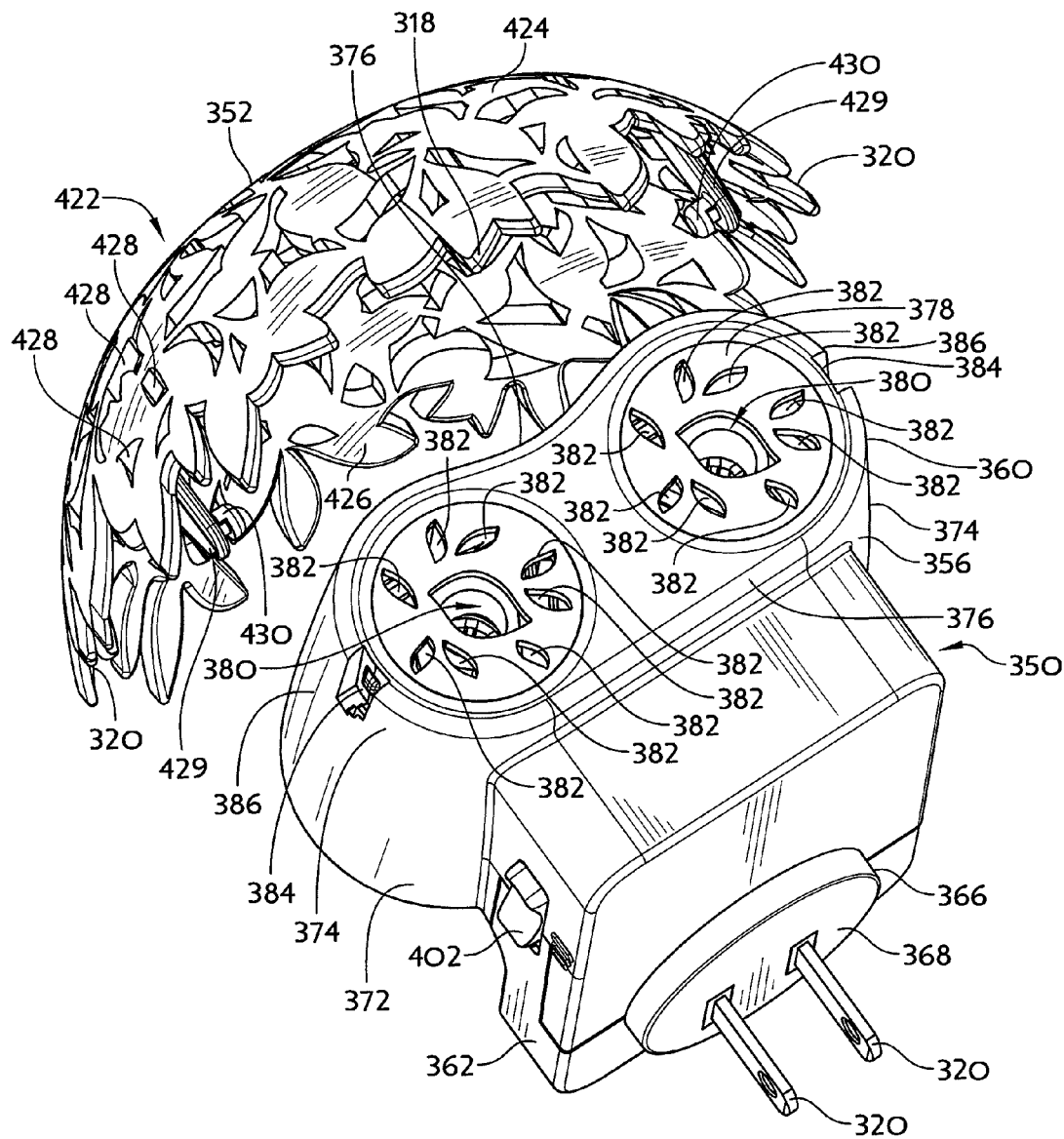
FIG. 10 is a top and rear perspective view of a second embodiment of a volatile material dispenser having a third embodiment of a faceplate attached thereto.
Figure 11:
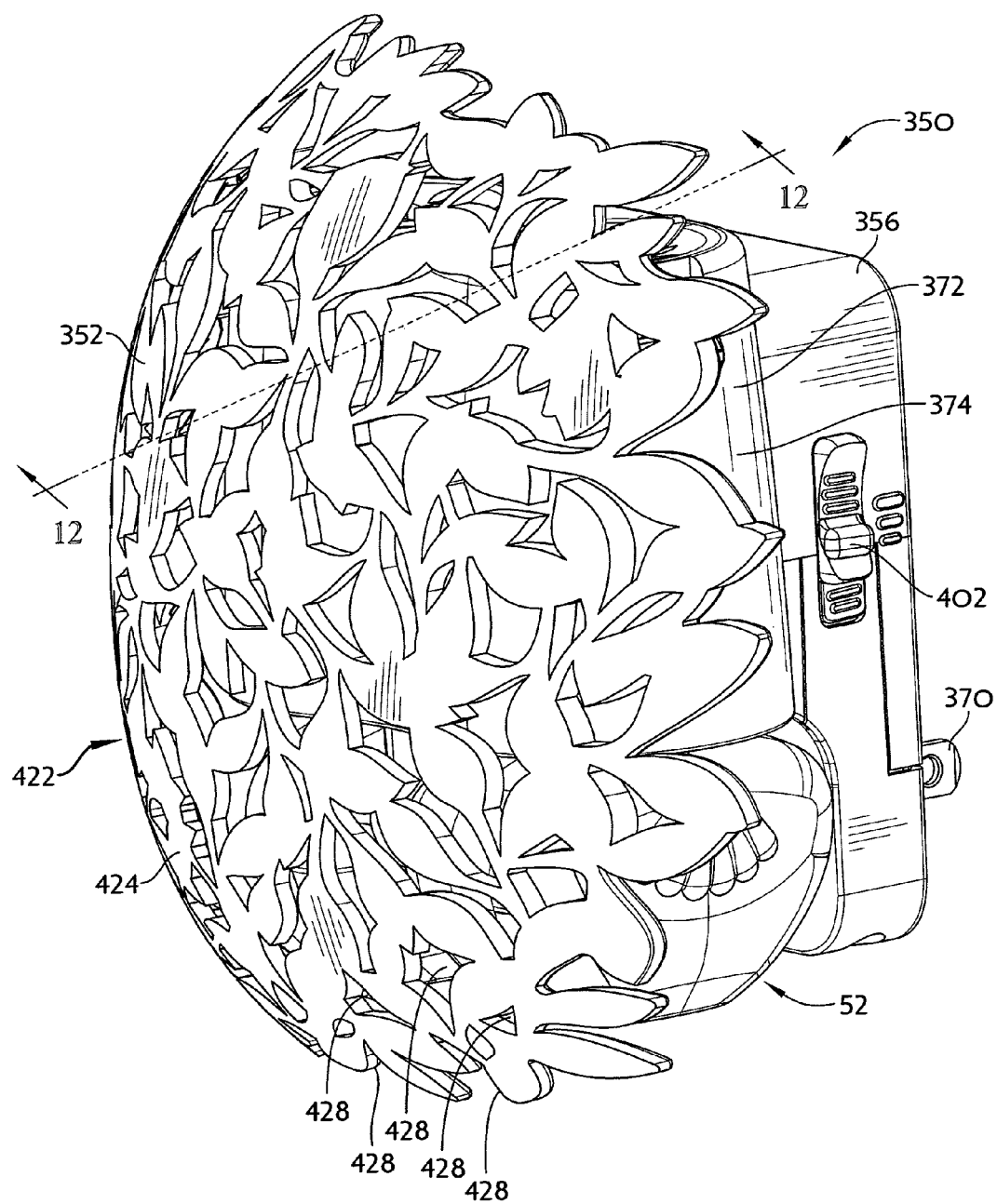
FIG. 11 is a top and front perspective view of the volatile material dispenser and the faceplate of FIG. 10.
Figure 12:
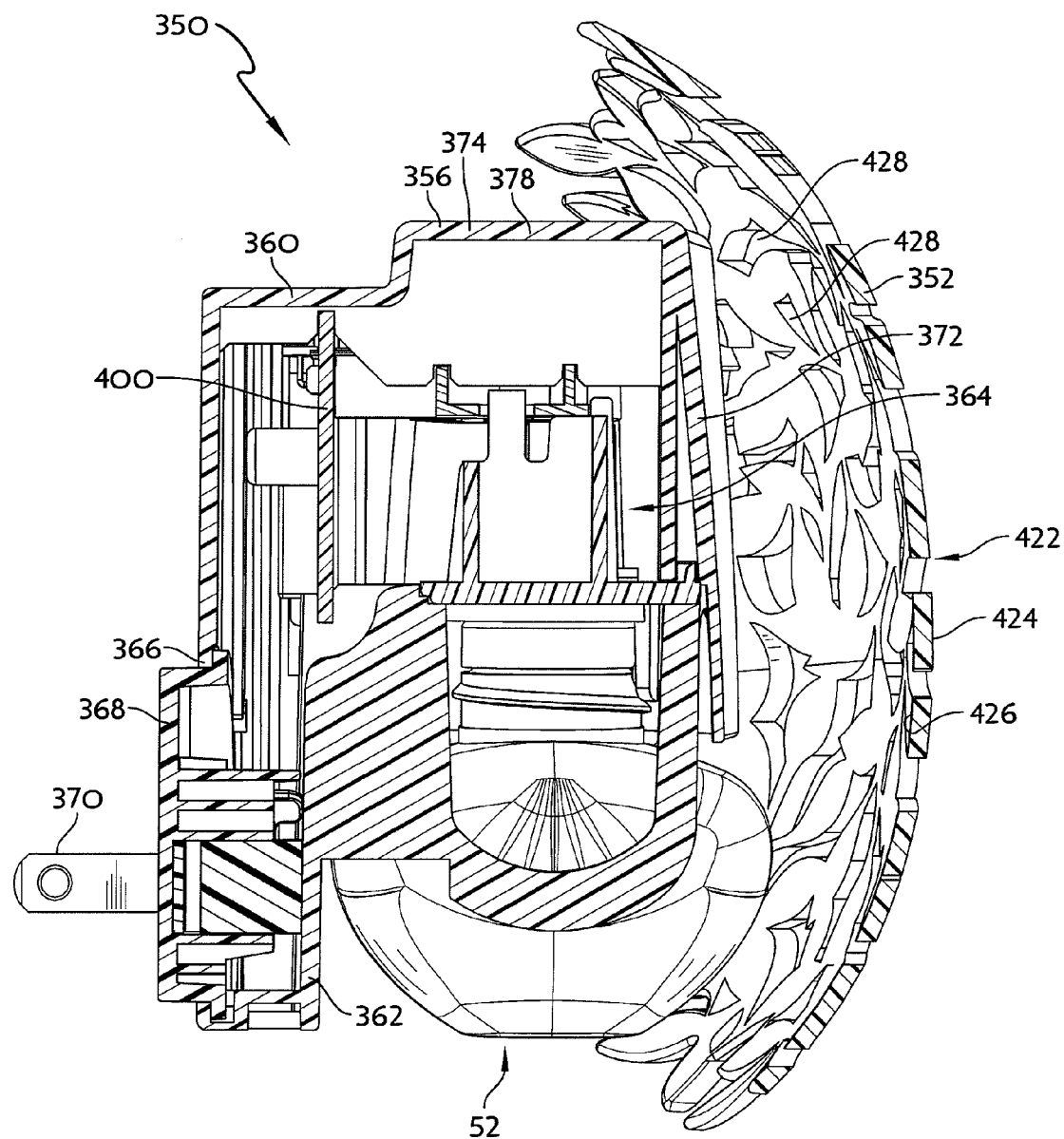
FIG. 12 is a cross-sectional view taken generally along the lines 12-12 of FIG. 11 and depicting how the faceplate of FIGS. 10 and 11 is spaced from a housing of the volatile material dispenser.
Figure 15:
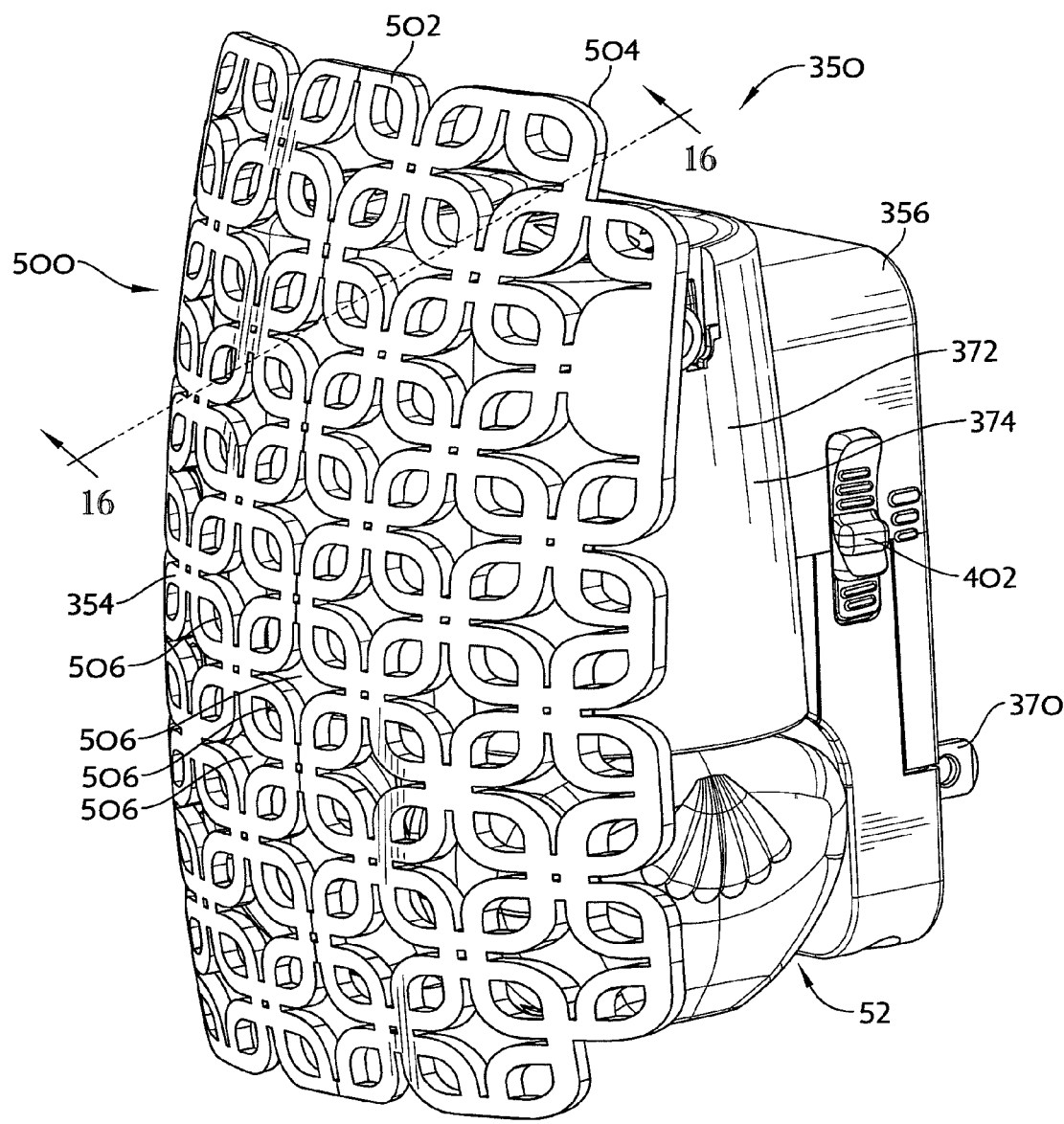
FIG. 15 is a top and front perspective view of the volatile material dispenser of FIG. 10 having a fourth embodiment of a faceplate attached thereto.
Figure 16:
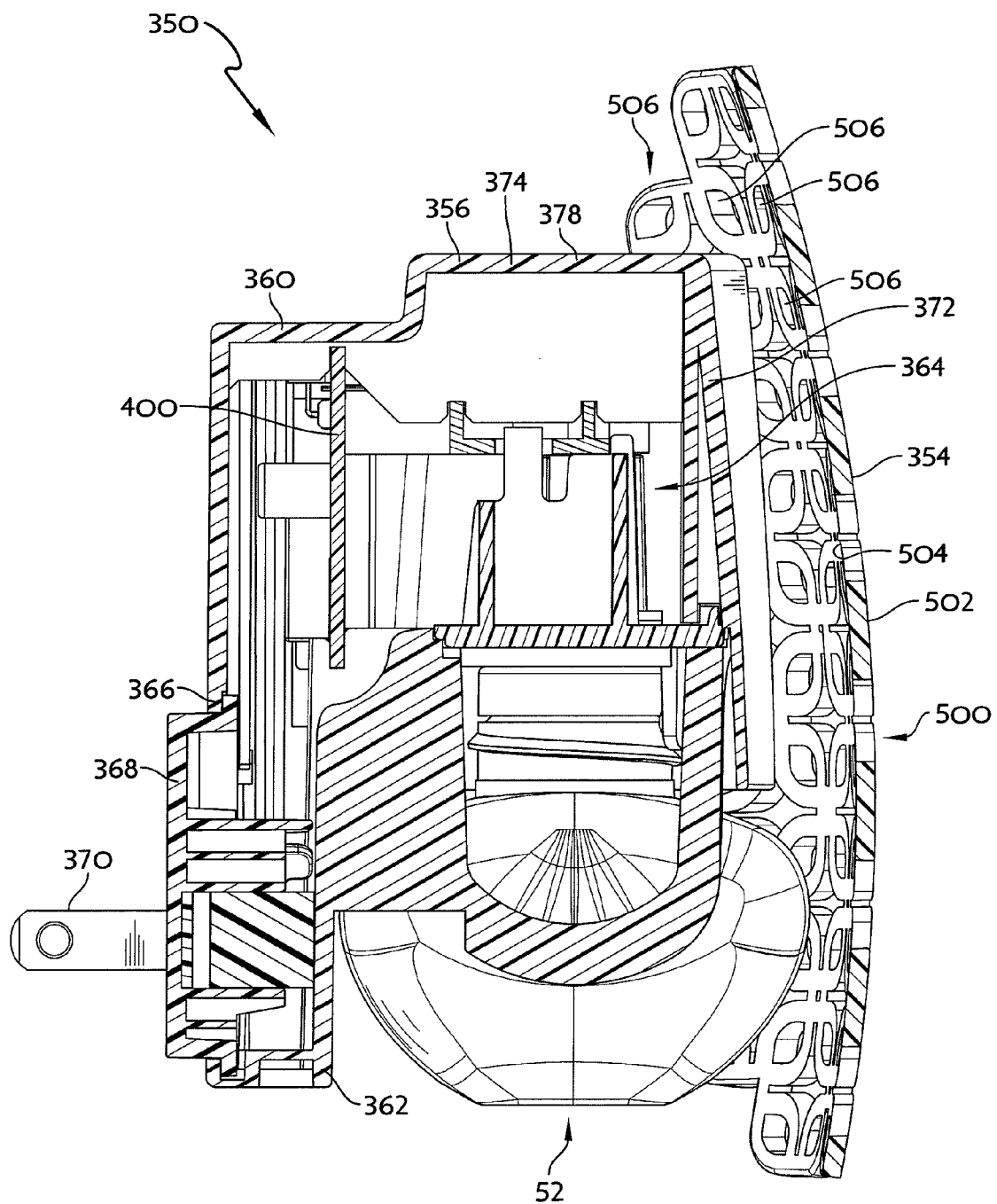
FIG. 16 is a cross-sectional view taken generally along the lines 16-16 of FIG. 15 and depicting how the faceplate of FIG. 15 is spaced from a housing of the volatile material dispenser.

A further embodiment of a dispenser 350 is depicted in FIGS. 10-14. One embodiment of a faceplate 352 similar to the faceplate 300 is depicted in FIGS. 10-12 and a further embodiment of a faceplate 354 similar to the faceplate 200 is depicted in FIGS. 15 and 16. The faceplates 352, 354 vary slightly from the faceplates 300, 200 in size, shape, and curvature. Specifically, the faceplates 352, 354 are designed to cover a larger dispenser 350, but are otherwise identical in function to the faceplates 300, 200 and, thus, the function of the apertures, spacing of the faceplates 300, 200, etc. will be identical.

Referring to FIGS. 10-14, the dispenser 350 includes a housing 356 that generally includes upper and lower portions 360, 362 attached to one another to form an interior chamber or cavity 364 therebetween. The upper and lower portions 360, 362 also join to form an aperture 366 at a rear portion of the housing 356 through which a plug assembly 368 extends, wherein the plug assembly includes electrical prongs 370 for insertion into a conventional outlet. While the plug assembly 368 is shown as being a conventional plug assembly for the United States, a plug assembly 368 adapted for use in any other country may be utilized. In addition, the plug assembly 368 may include any features known in the art, for example, the plug assembly 368 may be partially or fully rotatable.

The upper portion 360 of the housing 356, as best seen in FIGS. 10 and 12, includes an oblong side wall 372 having two generally cylindrical sections 374 connected by central sections 376. A top wall 378 encloses the oblong side wall 372 and includes two apertures 380 centered within each of the cylindrical sections 374 and a plurality of peripheral apertures 382 spaced from a periphery of the central apertures 380. Each of the apertures 380, 382 provides a means by which air and vaporized volatile material may move out of the housing 356. Two opposing grooves 384 are disposed in opposite sides 386 of the oblong side wall 372 and will be discussed in greater detail hereinafter.

Two heaters (not shown) similar to the heater 150 described above are situated within the cavity 364 of the housing 356 and positioned within each of the cylindrical sections 374. The volatile material dispenser 350 accommodates two refills 52, wherein the refills 52 are inserted into the housing 356 in a manner similar to that described above with respect to FIGS. 1 and 2. The refills 52 may also be retained within the housing 356 by one or more ledges, recesses, apertures, and the like that cooperate with the projections 76a, 76b. The heaters may be programmed to operate in an alternating manner, at the same time, or in any other suitable manner.

Similar to the volatile material dispenser 50 of FIGS. 1 and 2, the volatile material dispenser 350 further includes a circuit board 400 including suitable electronic circuitry for operating the volatile material dispenser 350. For example, the heaters may be connected to the circuit board 400 and one or more switches 402 may also be connected to the circuit board 400 to operate the heaters and/or other functionality of the dispenser 350. For example, the switches 402 may change a temperature of the heaters, change vaporization rates of the heaters, change a program that operates the heaters, turn the dispenser on and off, or may change any other feature or function of the heaters (or any other component of the volatile material dispenser 350). The circuit board 400 is connected by wires to the plug assembly 368, such that energy provided to the electrical prongs 370 operates the dispenser 350.

Referring to FIGS. 10-12, the volatile material dispenser 350 includes a faceplate 352 having a plurality of segments forming a pattern 422 that extends between front and rear surfaces 424, 426 of the faceplate 352. The pattern 422 is formed with a plurality of openings 428 (only some of which are labeled). Resilient arms 429 extend outwardly from the rear surface 426 of the faceplate 352 and include inwardly extending posts 430. The posts 430 are retained within the opposing grooves 384 disposed in opposite sides 386 of the oblong side wall 372.

Figure 13:
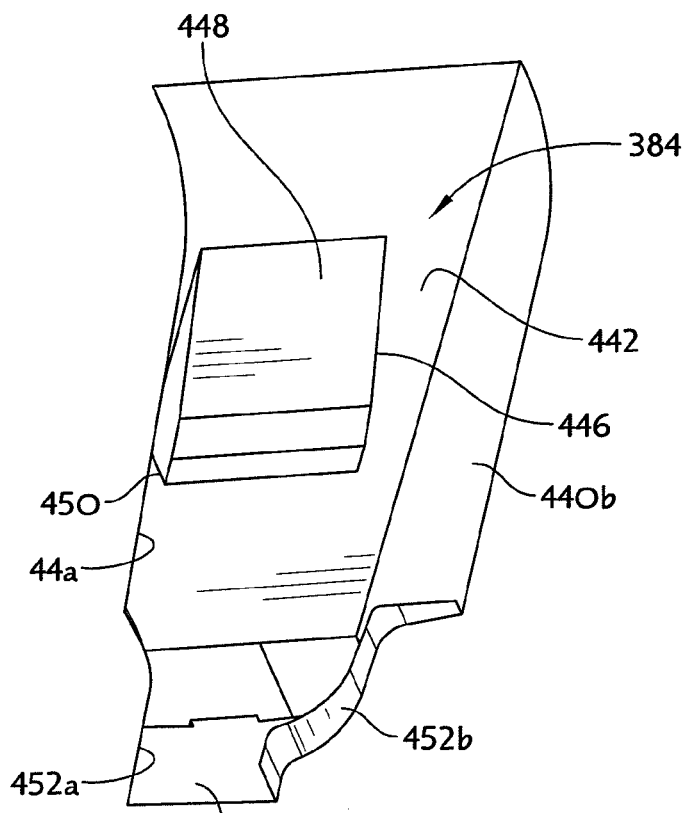
FIG. 13 is an enlarged perspective view of one of two grooves disposed within sides of the housing of the volatile material dispenser of FIGS. 10-12.

Referring to FIG. 13, the opposing grooves 384 extend downwardly from the top wall 378 of the housing 356 through the opposite sides 386 of the oblong side wall 372. Each groove 384 is generally rectangular and is formed by opposing side surfaces 440a, 440b, a rear surface 442, and a bottom surface 444. A projection 446 extends outwardly from the rear surface 442 and includes a ramped surface 448 that angles outwardly and downwardly and terminates at a downwardly facing surface 450 that is spaced from the bottom surface 444. A first curved wall 452a extends outwardly from the side surface 440a and a second curved wall 452b extends outwardly from the side surface 440b.

Figure 14:
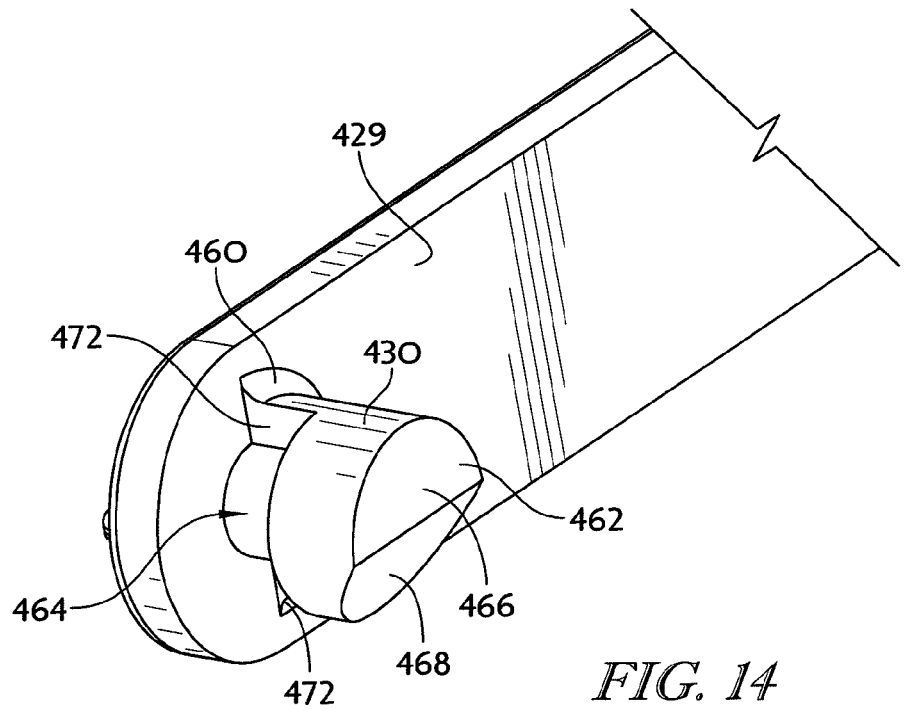
FIG. 14 is an enlarged perspective view of one of two arms extending outwardly from the faceplate of FIGS. 10-12 and including posts that are retained within the grooves of FIG. 13.

Each of the posts 430 extending from the arms 429, as seen in FIG. 14, includes a first end 460 extending from the arm 429 and a second, free end 462 opposite the first end 460. A semi-cylindrical cutout 464 is formed in the first end 460 of the post 430 adjacent the arm 429 and the second end 462 includes a generally flat surface 466 and an angled surface 468.

The faceplate 352 is attached to the dispenser 350 by sliding the posts 430 into the grooves 384. As the posts 384 are moved downwardly through the grooves, the angled surface 468 of each post 384 contacts a respective ramped surface 448 of the projections 446. The angled surface 468 rides up the ramped surface 448 until the post 430 passes the projection 446, wherein the second curved wall 452b enters the semi-cylindrical cutout 464 in the post 430, the first curved wall 452a abuts a side of the post 430 opposite the semi-cylindrical cutout 464, and the downwardly facing surface 450 of the projection 446 interferes with a side surface 470 of the post 430 to prevent linear movement of the post 430. In this position, the faceplate 352 may be rotated, but walls 472 forming the semi-circular cutout 464 provide stops to prevent over-rotation of the faceplate 352. The posts 430 may be removed from the grooves 384 by pulling outwardly and upwardly on the resilient arms 429.

Referring to FIGS. 15 and 16, the volatile material dispenser 350 includes a faceplate 354 having a plurality of segments forming a pattern 500 that extends between front and rear surfaces 502, 504 of the faceplate 354. The pattern 500 is formed with a plurality of openings 506 (only some of which are labeled). The faceplate 354 may have arms 429 that are attached to the dispenser 350 in a manner similar to the embodiment of FIGS. 10-14.

The open area, shape, structure, and other features of the faceplates 352, 354 are similar to the shape and apertures the faceplates 200, 300 described above. Further, any of the features, such as electrical components, described herein may be implemented within the faceplates 352, 354.

While arms 429 and posts 430 are depicted in the embodiments of FIGS. 10-16 as detachably attaching the faceplate 352 to the volatile material dispenser 350, any other suitable attachment mechanism may be utilized.

Although specific dispensers and refills are described with particularity herein, it is contemplated that the faceplates and other features thereof may be utilized in conjunction with any type of electrical or non-electrical dispenser and any type of refill and/or container. For example, the principles of the present invention may be utilized in conjunction with volatile material dispensers having one or more of a heater, a piezoelectric device, an aerosol actuator, or any other suitable volatile material dispensing mechanism. Examples of dispensers useful for the present disclosure include, but are not limited to, the dispensers described in Belongia et al. U.S. Pat. No. 7,840,123, Varanasi et al. U.S. Pat. No. 6,968,124, Beland et al. U.S. Patent Application Publication No. 2011/0049259, Zobele U.S. Patent Application Publication No. 2005/0180736, Pedrotti et al. U.S. Pat. No. 6,862,403, or any other suitable dispenser. The principles of the present invention may further be used with an aerosol can, a standalone refill, or any other housing that might be used to dispense a volatile material.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present invention provides volatile material dispensers having a faceplate removably attached thereto. The faceplates disclosed herein mask the overall look of the volatile material dispenser and provide a more pleasing look to the volatile material dispenser. The faceplates disclosed herein also do not increase a temperature or a volatile material output rate of the volatile material dispenser.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A volatile material dispenser, comprising:
   a housing including a top wall defining at least one aperture;
   a dispensing mechanism disposed within the housing for emitting a volatile material out of the at least one aperture;
   a faceplate including a front surface and a rear surface, wherein the faceplate includes a plurality of openings having a total open area that forms at least 20% of a total surface area of the faceplate; and
   at least one arm having a first end extending directly from the rear surface of the faceplate and a second end attached directly to the housing, wherein at least some of the plurality of openings surround the at least one arm.

2. The volatile material dispenser of claim 1, wherein the faceplate has a height dimension that spans at least a height of the dispenser and a width dimension that spans at least a width of the dispenser.

3. The volatile material dispenser of claim 2, wherein at least a portion of the housing has a contoured shape and the faceplate has a contoured shape to mimic a shape of the housing.

4. The volatile material dispenser of claim 2, wherein the volatile material dispenser is adapted to hold and retain a refill and, when the refill is disposed within the dispenser, the faceplate covers the refill when viewed from at least one direction.

5. The volatile material dispenser of claim 1, wherein the housing further includes at least one sidewall and the faceplate is attached to the at least one sidewall of the housing by the at least one arm such that the entire rear surface of the faceplate is spaced from and does not contact the housing.

6. The volatile material dispenser of claim 1, wherein the total open area formed by the plurality of openings forms at least 30% of a total surface area of the faceplate.

7. The volatile material dispenser of claim 1, wherein the faceplate is rotatably attached to the housing such that the faceplate may be rotated upwardly in an opening direction to access a refill when a refill is disposed within the housing and downwardly in a closing direction to cover the housing and refill when a refill is disposed within the housing, and wherein the faceplate covers the at least one aperture of the housing when rotated to provide access to the refill.

8. The volatile material dispenser of claim 7, further including a first stop for stopping rotational movement of the faceplate in the opening direction and a second stop for stopping rotational movement of the faceplate in the closing direction.

9. The volatile material dispenser of claim 1, wherein the faceplate includes a plurality of cutouts formed in one or more outer edges thereof that form a discontinuous outer peripheral edge of the faceplate.

10. A volatile material dispenser, comprising:
a housing including at least one sidewall and a top wall, wherein the top wall defines at least one aperture;
a dispensing mechanism disposed within the housing for emitting a volatile material out of the at least one aperture; and
a faceplate rotatably attached to the at least one sidewall of the housing and the faceplate including a plurality of openings forming a total open area in the faceplate, wherein at least a portion of the faceplate is spaced from the at least one sidewall of the housing to allow air flow between the at least one sidewall and the faceplate, wherein when the faceplate is rotated upwardly to a fully open position providing access to the housing, the faceplate covers the at least one aperture defined by the top wall, and when the faceplate is rotated downwardly to a fully closed position covering the housing, the faceplate does not cover the at least one aperture defined by the top wall.

11. The volatile material dispenser of claim 10, wherein at least one electrical component on the faceplate is electrically connected to a power supply or controller disposed within the housing.

12. The volatile material dispenser of claim 11, wherein the electrical component is in the form of one or more light sources that illuminate at least a portion of the faceplate.

13. The volatile material dispenser of claim 11, wherein the electrical component is in the form of a visual display or audible signal that may be selectively activated and deactivated.

14. The volatile material dispenser of claim 10, wherein the faceplate includes a plurality of cutouts formed in one or more outer edges thereof that form a discontinuous outer peripheral edge of the faceplate.

15. The volatile material dispenser of claim 10, wherein the total open area of the faceplate forms at least 20% of a total surface area of the faceplate.

16. A volatile material dispenser, comprising:
a housing including at least one sidewall and a top wall, wherein the top wall defines at least one aperture;
a refill containing a volatile material, the refill disposed within the housing;
a dispensing mechanism disposed within the housing that emits the volatile material from the refill out of the at least one aperture; and
a faceplate including at least one arm rotatably attached to the at least one sidewall of the housing, wherein a volatile material output of the dispenser with the faceplate attached thereto is substantially the same as the volatile material output of the dispenser without the faceplate attached thereto, wherein when the faceplate is rotated upwardly to a fully open position providing access to the refill, the faceplate covers the at least one aperture defined by the top wall, and when the faceplate is rotated downwardly to a fully closed position at least partially covering the refill, the faceplate does not cover the at least one aperture defined by the top wall.

17. The volatile material dispenser of claim 16, wherein at least a portion of the faceplate is spaced from the housing to allow air flow between the at least one sidewall of the housing and the faceplate.

18. The volatile material dispenser of claim 17, wherein the faceplate includes a plurality of apertures disposed therethrough, wherein the plurality of apertures creates a total open area within the faceplate that forms at least 20% of a total surface area of the faceplate.

19. The volatile material dispenser of claim 16, wherein the faceplate includes a plurality of cutouts formed in one or more outer edges thereof that form a discontinuous outer peripheral edge of the faceplate.

20. The volatile material dispenser of claim 16, wherein the faceplate has a height dimension that spans at least a height of the dispenser and a width dimension that spans at least a width of the dispenser and at least a portion of the housing has a contoured shape and the faceplate has a contoured shape to mimic a shape of the housing.

* * * * *